(12) United States Patent
Bohnhoff

(10) Patent No.: US 9,314,542 B2
(45) Date of Patent: Apr. 19, 2016

(54) METHOD FOR STERILIZING SURGICAL BATTERIES

(76) Inventor: Phillip Bohnhoff, Rowlett, TX (US)

(*) Notice: Subject to any disclaimer, the term of this patent is extended or adjusted under 35 U.S.C. 154(b) by 0 days.

(21) Appl. No.: 13/385,056

(22) Filed: Jan. 31, 2012

(65) Prior Publication Data

US 2014/0030145 A1    Jan. 30, 2014

(51) Int. Cl.
*A61L 2/16* (2006.01)
*A61L 2/07* (2006.01)
*A61L 2/26* (2006.01)

(52) U.S. Cl.
CPC ... *A61L 2/07* (2013.01); *A61L 2/26* (2013.01); *A61L 2202/21* (2013.01)

(58) Field of Classification Search
CPC .................................. A61L 2/16; A61L 2/07
USPC ................................................ 422/22, 292, 28
See application file for complete search history.

(56) References Cited

U.S. PATENT DOCUMENTS

| | | | |
|---|---|---|---|
| 5,505,916 A * | 4/1996 | Berry, Jr. | 422/300 |
| 5,540,901 A * | 7/1996 | Riley | 422/300 |
| 5,599,512 A * | 2/1997 | Latulippe et al. | 422/300 |
| 5,720,930 A * | 2/1998 | Bean | 422/300 |
| 2003/0160590 A1* | 8/2003 | Schaefer et al. | 320/107 |
| 2005/0238530 A1* | 10/2005 | Frieze et al. | 422/1 |
| 2007/0048176 A1* | 3/2007 | Orrico | 422/29 |
| 2008/0215062 A1* | 9/2008 | Bowen et al. | 606/108 |
| 2009/0146032 A1* | 6/2009 | Bettenhausen et al. | 248/220.31 |
| 2010/0176016 A1* | 7/2010 | Pell | 206/370 |
| 2013/0319888 A1* | 12/2013 | Birkbeck et al. | 206/370 |

\* cited by examiner

*Primary Examiner* — Sean E Conley
(74) *Attorney, Agent, or Firm* — Thrasher Associates

(57) ABSTRACT

The invention is an apparatus for sterilizing surgical batteries.

3 Claims, 2 Drawing Sheets

METHOD FOR STERILIZING SURGICAL BATTERIES

CLAIM OF PRIORITY

This Application claims priority to U.S. Provisional Patent Application No. 61/462,132 to common inventor Bohnhoff, dated 28, Jan. 2011 and entitled Sterilization Tray for Surgical Instruments and Batteries.

FIELD OF THE INVENTION

The present invention relates generally to the sterilization of medical batteries.

PROBLEM STATEMENT

Interpretation Considerations

This section describes the technical field in more detail, and discusses problems encountered in the technical field. This section does not describe prior art as defined for purposes of anticipation or obviousness under 35 U.S.C. section 102 or 35 U.S.C. section 103. Thus, nothing stated in the Problem Statement is to be construed as prior art.

Discussion

The medical field requires sterilization of equipment to reduce the spread of infections. Instruments that enter a surgical area must be sterilized to a high sterility assurance level, or SAL. Examples of such instruments include batteries used in medical equipment.

Currently, a technician must spend a large amount of time sterilizing and vacuum sealing batteries for future surgeries. The sterilization process can take several minutes for each battery, and the sterilization process can only accommodate one battery to be packaged and sealed in a package at a time. Additionally, different surgeries require a different number of batteries, and surgical technicians must adjust their calendar to fit these requirements.

During surgery, a technician must open the disposable vacuum sealed pouches (also called "wraps") for each battery needed, and the vacuum sealed pouches take some time to open. During surgeries that require multiple batteries, the disposal waste from these packages can accumulate becoming problematic. The technician also dedicates valuable time to accounting for these surgical battery wraps that would be better spent elsewhere. Accordingly, there is a need to reduce the time required to sterilize surgical batteries and also a need to reduce the accumulation of the wraps. The present invention solves both of these problems.

BRIEF DESCRIPTION OF THE DRAWINGS

Various aspects of the invention, as well as an embodiment, are better understood by reference to the following detailed description. The detailed description, given by way of examples and not intended to limit the present invention solely thereto, will be better understood when read in conjunction with the drawings wherein like reference numerals denote like elements and parts in which.

EXEMPLARY EMBODIMENT OF A BEST MODE

Interpretation Considerations

Figure 1:
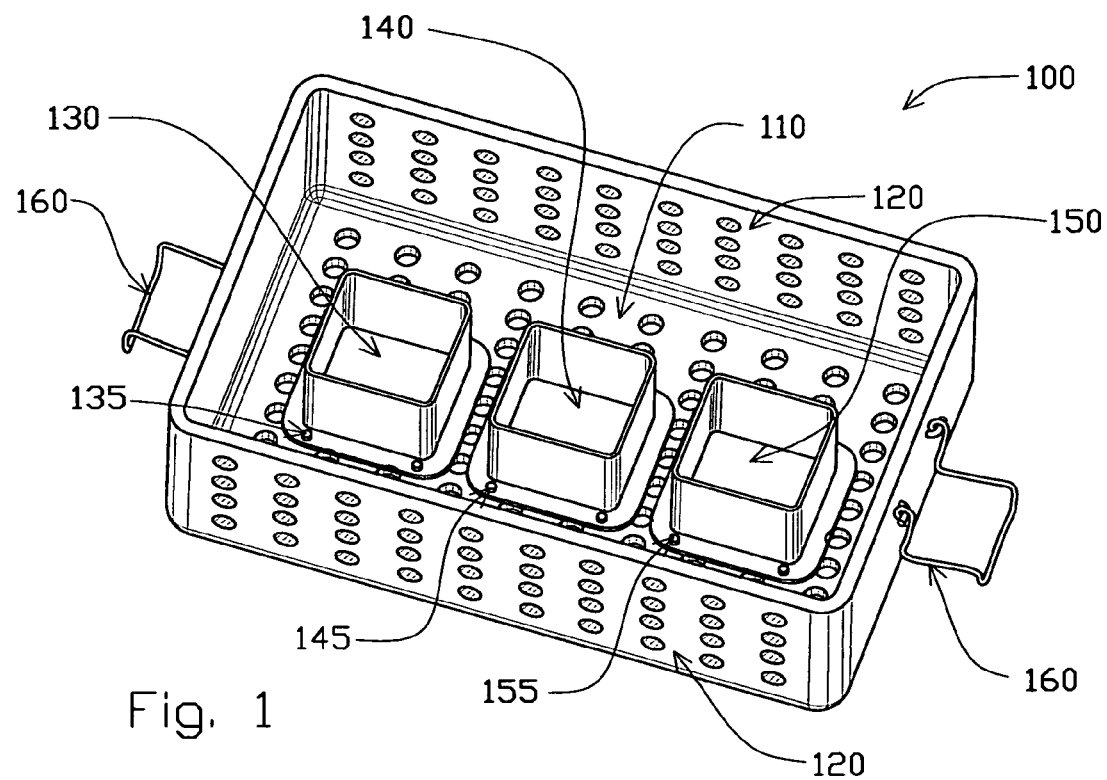
FIG. 1 is an isometric view of the front side, the top side, and the inside of the tray.

When reading this section (An Exemplary Embodiment of a Best Mode, which describes an exemplary embodiment of the best mode of the invention, hereinafter "exemplary embodiment"), one should keep in mind several points. First, the following exemplary embodiment is what the inventor believes to be the best mode for practicing the invention at the time this patent was filed. Thus, since one of ordinary skill in the art may recognize from the following exemplary embodiment that substantially equivalent structures or substantially equivalent acts may be used to achieve the same results in exactly the same way, or to achieve the same results in a not dissimilar way, the following exemplary embodiment should not be interpreted as limiting the invention to one embodiment.

Likewise, individual aspects (sometimes called species) of the invention are provided as examples, and, accordingly, one of ordinary skill in the art may recognize from a following exemplary structure (or a following exemplary act) that a substantially equivalent structure or substantially equivalent act may be used to either achieve the same results in substantially the same way, or to achieve the same results in a not dissimilar way.

Accordingly, the discussion of a species (or a specific item) invokes the genus (the class of items) to which that species belongs as well as related species in that genus. Likewise, the recitation of a genus invokes the species known in the art. Furthermore, it is recognized that as technology develops, a number of additional alternatives to achieve an aspect of the invention may arise. Such advances are hereby incorporated within their respective genus, and should be recognized as being functionally equivalent or structurally equivalent to the aspect shown or described.

Second, the only essential aspects of the invention are identified by the claims. Thus, aspects of the invention, including elements, acts, functions, and relationships (shown or described) should not be interpreted as being essential unless they are explicitly described and identified as being essential. Third, a function or an act should be interpreted as incorporating all modes of doing that function or act, unless otherwise explicitly stated (for example, one recognizes that "tacking" may be done by nailing, stapling, gluing, hot gunning, riveting, etc., and so a use of the word tacking invokes stapling, gluing, etc., and all other modes of that word and similar words, such as "attaching").

Fourth, unless explicitly stated otherwise, conjunctive words (such as "or", "and", "including", or "comprising" for example) should be interpreted in the inclusive, not the exclusive, sense. Fifth, the words "means" and "step" are provided to facilitate the reader's understanding of the invention and do not mean "means" or "step" as defined in §112, paragraph 6 of 35 U.S.C., unless used as "means for -functioning-" or "step for -functioning-" in the Claims section. Sixth, the invention is also described in view of the Festo decisions, and, in that regard, the claims and the invention incorporate equivalents known, unknown, foreseeable, and unforeseeable. Seventh, the language and each word used in the invention should be given the ordinary interpretation of the language and the word, unless indicated otherwise. As will be understood by those of ordinary skill in the art, various structures and devices are depicted in block diagram form in order to avoid unnecessarily obscuring the invention.

It should be noted in the following discussion that acts with like names are performed in like manners, unless otherwise stated. Of course, the foregoing discussions and definitions are provided for clarification purposes and are not limiting. Words and phrases are to be given their ordinary plain meaning unless indicated otherwise.

DETAILED DESCRIPTION OF THE DRAWINGS

Sterilization is performed by many methods. For example, the "Flash" Autoclave uses the gravity displacement sterilizer which operates at a temperature of 270-272° F. (132-134° C.). The batteries are placed unwrapped in an instrument tray or basket. The tray ensures that none of the batteries will touch the terminals. There is a three-minute exposure time of the batteries to the sterilizer. Following the sterilization, there is no dry time. Batteries sterilized with this method have to be utilized immediately and cannot be stored.

Another sterilization method is the Hi-Vac method. This method uses a pre-vacuumed sterilizer which operates at the same temperature as the "Flash" Autoclave 270-272° F. (132-134° C.). In this sterilization method, the batteries may be wrapped or unwrapped. There is a four-minute exposure time of the batteries to the sterilizer. Following the sterilization, there is no dry time. Batteries sterilized with this method have to be utilized immediately and cannot be stored.

Another sterilization method is the Ethylene Oxide method, ETO. The ETO is 100% ETO and operates at a temperature of 120-135° F. (49-57° C.). This method requires the instrument wrapped in a tray or fully perforated sterilization box. There is a one hour exposure time followed by an eight-hour (usually minimum) aeration time. The battery packs sterilized using the ETO method will run approximately 20% less time than battery packs sterilized by the "Flash" method.

Another method of sterilization is low temperature gas plasma sterilization. STERRAD® Gas Plasma is a developed method by Johnson & Johnson Company. The sterilization is performed per the manufacturer's user instructions. This method is a low temperature sterilization method. Using this sterilization process allows the batteries to be stored following the sterilization process. The batteries maintain a higher charge following this method versus the methods described above.

In one embodiment, shown in FIG. 1, the invention is a medical battery sterilization tray 100. The tray can include an air-permeable base 110 and sides 120. A first battery lock 130 is secured to the base 110. A second battery lock 140 is secured to the base 110 next to the first battery lock 130. The first battery lock 130 is affixed to the base 110 with several pins 135. The second battery lock 140 is also affixed to the base 110 with pins 145. The inventive tray 100 can include one, two, or three battery locks. In a larger embodiment, the tray can include more than three battery locks. The tray 100 includes a third batter lock 150 which is also affixed to the base 100 with pins 155. Alternative couplers can be used as an alternative to the pins such as bolts, screws, plugs, and clips. Another way to affix the battery locks is to weld the locks to the tray 100. The tray 100 has two handles 160 secured to the top of the sides 110 of the tray 100 for easier handling control and carrying of the tray 100. The batteries (not shown but understood by those with ordinary skill in the art) are placed in the battery locks 130, 140, 150, which secure the batteries for the sterilization process.

Figure 2:
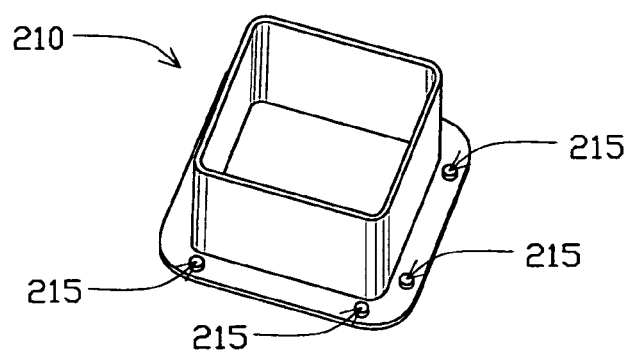
FIG. 2 is a top view of the one of the battery locks.

Shown in FIG. 2 is one of the battery locks used in with the tray. The battery lock 210 locks the battery inside the lock 210. The battery lock 210 has pins 215 to hold the battery lock 210 to the tray. The battery lock 210 has pins 215 on all four sides. Only two sides are shown in FIG. 2, but the other sides can be determined by those with ordinary skill in the art.

Figure 3:
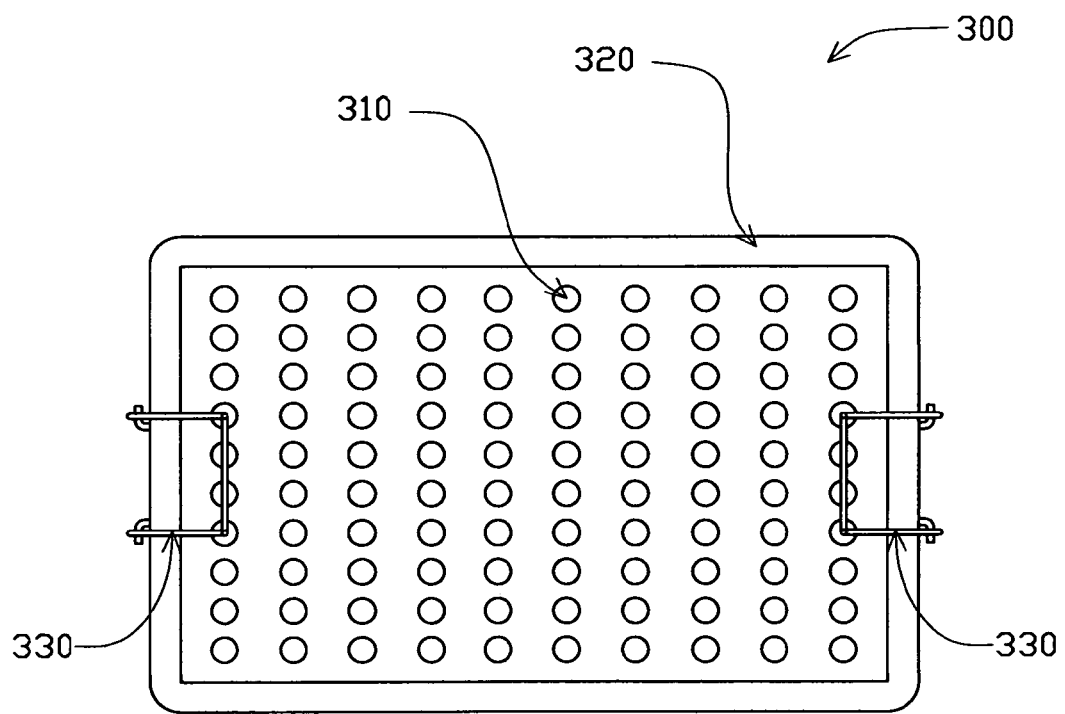
FIG. 3 is a top view of the lid.

Shown in FIG. 3 is the lid 300 that accompanies tray in FIG. 1. The lid 300 secures to the tray. The lid 300 is air-permeable, similar to the tray. The holes 310 allow the sterilization gas to infiltrate the tray to sterilize the medical batteries. The lid 310 has a rim 320 that affixes to the top of the sides of the tray. The handles 330 of the tray clamp over the top of the lid 310 to secure it.

The tray with the batteries is wrapped by technicians. Once wrapped, the batteries are sterilized. The wrap stores the batteries so that they stay sterilized and increase the life of the batteries. With the invention, when the technician needs three batteries, the technician un-wraps one container which contains three batteries. Accordingly, this inventive tray reduces the clutter of opened wrap waste in the operating room, the time needed to make ready batteries, and the time needed to sterilize batteries.

The invention is also a method of sterilizing medical batteries. The method includes the acts of affixing a plurality of medical batteries in a plurality of battery locks, protecting the plurality of sterilized batteries by enveloping them with a medical-grade wrap, and then exposing the medical batteries to a sterilizer. Next, the method ends the act of exposing to provide a user a plurality of sterilized batteries. The batteries are affixed to an apparatus such as the medical sterilization tray. The batteries are first affixed to the tray, which is then encased in a wrap (or other container) which is preferably a medical-grade. When wrapped, the tray with the batteries is placed in a sterilizer. The batteries are then sterilized and prepared for surgery. The preferred sterilizer is a Sterrad sterilizer.

Though the invention has been described with respect to a specific preferred embodiment, many advantages, variations and modifications will become apparent to those skilled in the art upon reading the present application. It is therefore the intention that the appended claims and their equivalents be interpreted as broadly as possible in view of the prior art to include all such variations and modifications.

I claim:

1. A method of sterilizing medical batteries, comprising:
   affixing a plurality of medical batteries in a plurality of battery locks maintained in a sterilization tray;
   each battery lock comprises
      at least four sides that contour to substantially an entire perimeter of a medical battery, the sides for securing the battery into the battery lock, a base coupled to the at least four sides, the base having a top and a bottom, the top being defined as the side of the base being coupled to the at least four sides, and at least two pins coupled to the bottom of the base, the at least two pins sized to securely couple to a modular sterilization tray via holes;
   protecting a plurality of sterilized batteries by enveloping said sterilized batteries with a vacuum sealed wrap;
   exposing the medical batteries to a sterilizer;
   ending the act of exposing to have a plurality of sterilized batteries.

2. The method in claim 1, wherein the sterilizer is a low temperature gas plasma sterilizer.

3. The method of claim 2, wherein the low temperature gas plasma sterilizer is a Sterrad sterilizer.

* * * * *